(12) United States Patent
Govari et al.

(10) Patent No.: US 11,794,004 B2
(45) Date of Patent: Oct. 24, 2023

(54) ELECTROPORATION WITH COOLING

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 356 days.

(21) Appl. No.: 16/897,886

(22) Filed: Jun. 10, 2020

(65) Prior Publication Data

US 2021/0386996 A1    Dec. 16, 2021

(51) Int. Cl.
| | |
|---|---|
| A61N 1/05 | (2006.01) |
| A61B 5/283 | (2021.01) |
| A61B 5/00 | (2006.01) |
| A61N 1/32 | (2006.01) |

(52) U.S. Cl.
CPC ............ *A61N 1/0565* (2013.01); *A61B 5/283* (2021.01); *A61B 5/6856* (2013.01); *A61N 1/327* (2013.01)

(58) Field of Classification Search
CPC ...... A61N 1/0565; A61N 1/327; A61B 5/283; A61B 5/6856
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron |
| 6,332,089 B1 | 12/2001 | Acker |
| 6,416,505 B1 | 7/2002 | Fleischman |
| 6,484,118 B1 | 11/2002 | Govari |
| 6,618,612 B1 | 9/2003 | Acker |
| 6,690,963 B2 | 2/2004 | Ben-Haim |

(Continued)

FOREIGN PATENT DOCUMENTS

| | | |
|---|---|---|
| EP | 2783652 A2 | 10/2014 |
| WO | WO1996005768 A1 | 2/1996 |

(Continued)

OTHER PUBLICATIONS

European Search Report for corresponding EPA No. 21178404.6 dated Nov. 9, 2021.

(Continued)

*Primary Examiner* — Mallika D Fairchild

(57) ABSTRACT

A medical system includes a catheter including an insertion tube having a distal end, an elongated resilient distal section fixed to the distal end of the insertion tube, the distal section having an outer surface, and a plurality of electrode structures, each electrode structure being disposed on, and bulging above the outer surface of the distal section, each electrode structure including a respective primary electrode and at least one respective secondary electrode extending around the outer surface, and respective electrically insulating material disposed around the outer surface and between the respective primary electrode and the at least one respective secondary electrode, the respective primary electrode bulging further above the outer surface than the at least one respective secondary electrode and the electrically insulating material.

16 Claims, 6 Drawing Sheets

(56) References Cited

U.S. PATENT DOCUMENTS

| | | |
|---|---|---|
| 7,756,576 B2 | 7/2010 | Levin |
| 7,848,787 B2 | 12/2010 | Osadchy |
| 7,869,865 B2 | 1/2011 | Govari |
| 8,048,067 B2 | 11/2011 | Davalos |
| 8,221,411 B2 | 7/2012 | Francischelli |
| 9,149,198 B2 | 10/2015 | Werneth |
| 10,039,467 B2 | 8/2018 | Stewart |
| 10,271,893 B2 | 4/2019 | Stewart |
| 10,342,598 B2 | 7/2019 | Long |
| 10,531,914 B2 | 1/2020 | Stewart |
| 2002/0006455 A1 | 1/2002 | Levine |
| 2002/0065455 A1 | 5/2002 | Ben-Haim |
| 2003/0045831 A1 | 3/2003 | Ponzi |
| 2003/0120150 A1 | 6/2003 | Govari |
| 2004/0068178 A1 | 4/2004 | Govari |
| 2010/0168548 A1 | 7/2010 | Govari |
| 2011/0028820 A1* | 2/2011 | Lau ............... A61B 5/6858 606/41 |
| 2012/0310065 A1 | 12/2012 | Falwell |
| 2013/0345698 A1* | 12/2013 | Govari ............ A61B 18/1492 606/41 |
| 2015/0328448 A1 | 11/2015 | Richter |
| 2016/0051324 A1 | 2/2016 | Stewart |
| 2016/0143689 A1* | 5/2016 | Ditter ............. A61B 5/287 606/46 |
| 2016/0324575 A1 | 11/2016 | Panescu |
| 2019/0125422 A1* | 5/2019 | Babkin ............ A61B 18/02 |

FOREIGN PATENT DOCUMENTS

| | | | |
|---|---|---|---|
| WO | WO-2019036653 A2 * | 2/2019 | ......... A61B 18/1492 |
| WO | WO2019036653 A2 | 2/2019 | |

OTHER PUBLICATIONS

European Search Report for corresponding EPA No. 21178404.6 dated Jan. 18, 2022.

* cited by examiner

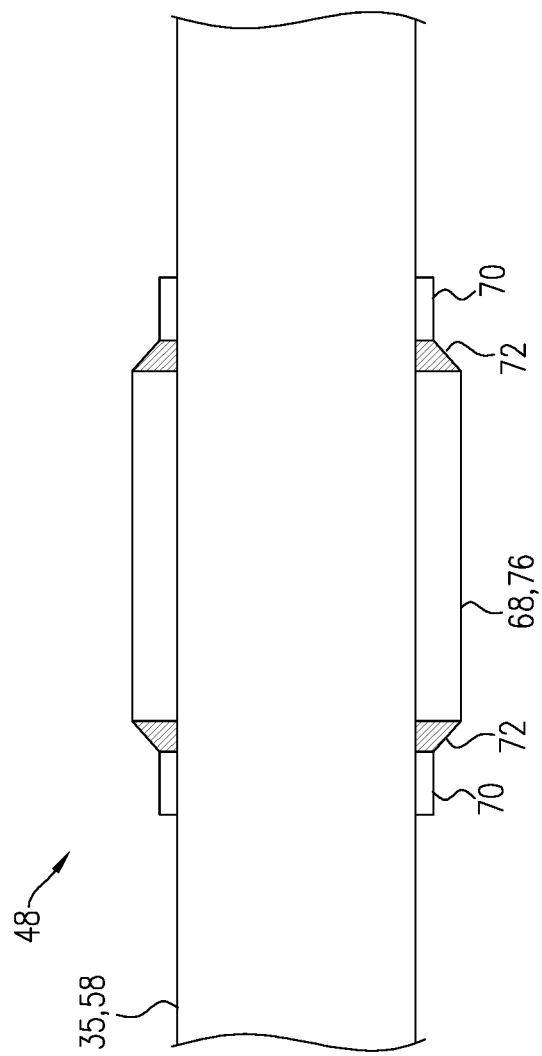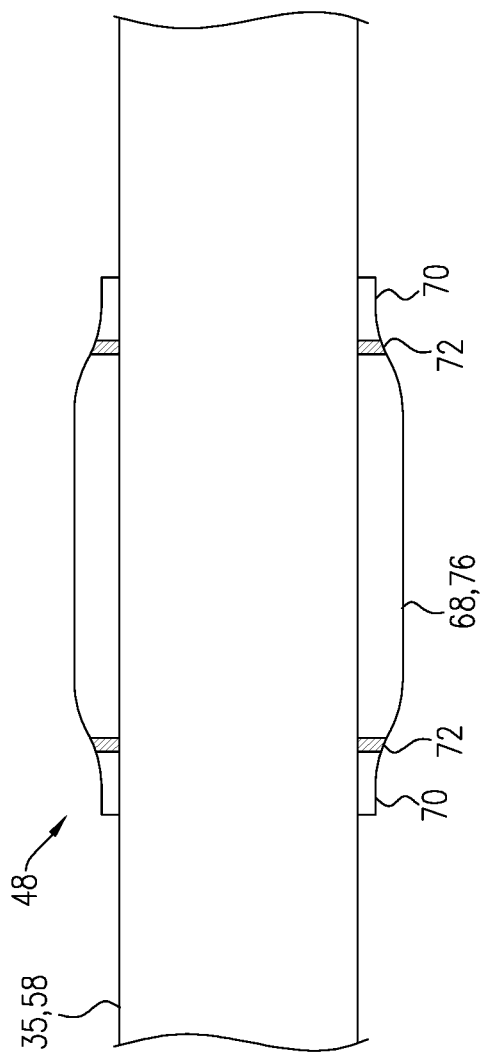

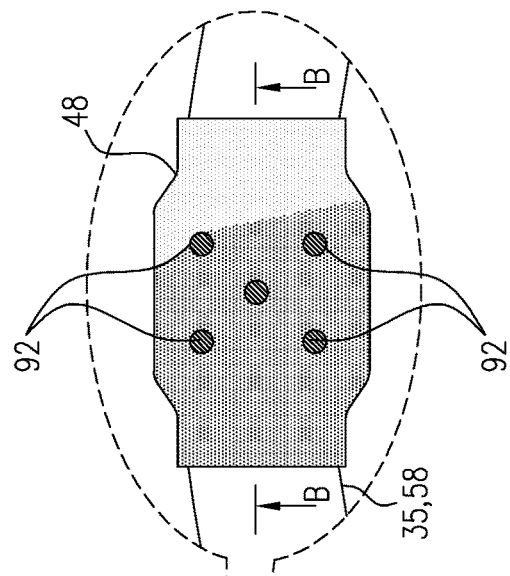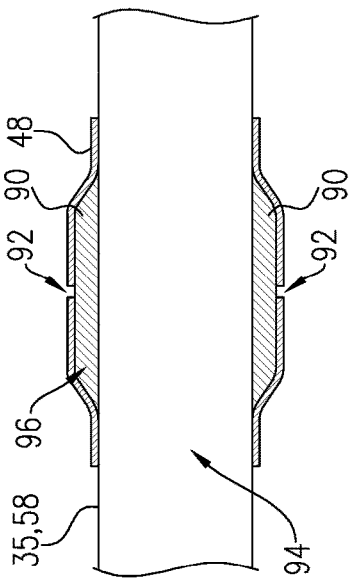
FIG. 5
FIG. 6

ELECTROPORATION WITH COOLING

FIELD OF THE INVENTION

The present invention relates to medical systems, and in particular, but not exclusively to, catheter devices.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/006455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied through the tip electrode(s) of the ablating catheter, and current flows through the media that surrounds it, i.e., blood and tissue, between the tip electrode(s) and an indifferent electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

US Patent Publication No. 2010/0168548 to Govan, et al., describes cardiac catheters, including a lasso catheter, for use in a system for electrical mapping of the heart. The catheter has an array of raised, perforated electrodes, which are in fluid communication with an irrigating lumen. There are position sensors on a distal loop section and on a proximal base section of the catheter. The electrodes are sensing electrodes that may be adapted for pacing or ablation. The raised electrodes securely contact cardiac tissue, forming electrical connections having little resistance.

US Patent Publication No. 2012/0310065 to Falwell, et al., describes apparatus and methods for mapping electrical activity within the heart, creating lesions in the heart tissue (ablating) to create a region of necrotic tissue which serves to disable the propagation of errant electrical impulses caused by an arrhythmia.

US Patent Publication No. 2016/0324575 to Panescu, et al., describes a medical instrument (for example, an ablation device) comprising an elongate body having a proximal end and a distal end, an energy delivery member positioned at the distal end of the elongate body, a first plurality of temperature-measurement devices carried by or positioned within the energy delivery member, the first plurality of temperature-measurement devices being thermally insulated from the energy delivery member, and a second plurality of temperature-measurement devices positioned proximal to a proximal end of the energy delivery member, the second plurality of temperature-measurement devices being thermally insulated from the energy delivery member.

U.S. Pat. No. 6,416,505 to Fleischman, et al., describes a surgical method and apparatus for positioning a diagnostic or therapeutic element within the body. The apparatus may be catheter-based or a probe including a relatively short shaft.

U.S. Pat. No. 6,482,202 to Goble, et al., describes an electrosurgical instrument, which is used for the treatment of tissue in the presence of an electrically-conductive fluid medium, and comprises an instrument shaft, and an electrode assembly at one end of the shaft. The electrode assembly comprises a tissue treatment electrode and a return electrode which is electrically insulated from the tissue treatment electrode by means of an insulation member. The tissue treatment electrode has an exposed end for treating tissue, and the return electrode has a fluid contact surface which is spaced from the tissue treatment electrode in such a manner as to define, in use, a conductive fluid path that completes an electrical circuit between the tissue treatment electrode and the return electrode. The electrode assembly is provided with a plurality of apertures in the region of the tissue treatment electrode, through which apertures vapor bubbles and/or particulate material can be aspirated from the region surrounding the tissue treatment electrode.

SUMMARY

There is provided in accordance with an embodiment of the present invention, a medical system including a catheter including an insertion tube having a distal end, an elongated resilient distal section fixed to the distal end of the insertion tube, the distal section having an outer surface, and a plurality of electrode structures, each electrode structure being disposed on, and bulging above the outer surface of the distal section, each electrode structure including a respective primary electrode and at least one respective secondary electrode extending around the outer surface, and respective electrically insulating material disposed around the outer surface and between the respective primary electrode and the at least one respective secondary electrode, the respective primary electrode bulging further above the outer surface than the at least one respective secondary electrode and the respective electrically insulating material.

Further in accordance with an embodiment of the present invention the insertion tube is configured for insertion through a blood vessel into a heart of a subject, and wherein the resilient distal section defines a loop when deployed within the heart, and is configured to open and close the loop.

Still further in accordance with an embodiment of the present invention the loop has a diameter of between 5 mm and 35 mm.

Additionally, in accordance with an embodiment of the present invention the respective primary electrode includes a metal ring and the at least one respective secondary electrode includes at least one metal ring, the respective primary electrode and the at least one respective secondary electrode being connected by the respective electrically insulating material.

Moreover, in accordance with an embodiment of the present invention the at least one respective secondary electrode includes two respective electrodes.

Further in accordance with an embodiment of the present invention the two respective electrodes are disposed on either side of the respective primary electrode.

Still further in accordance with an embodiment of the present invention the distal section has a direction of elongation, the respective primary electrode having a first width measured parallel to the direction of elongation, each of the two respective electrodes having a second width measured parallel to the direction of elongation, the first width being greater than the second width.

Additionally, in accordance with an embodiment of the present invention the first width is at least twice the size of the second width.

Moreover, in accordance with an embodiment of the present invention the first width is in a range of 2 mm to 8 mm and the second width is in a range of 0.1 mm to 1 mm.

Further in accordance with an embodiment of the present invention the distal section has a direction of elongation, each electrode structure having a width measured parallel to the direction of elongation of between 2.5 mm and 10 mm.

Still further in accordance with an embodiment of the present invention each electrode structure includes respective thermally conductive material disposed under the respective primary electrode, between the respective primary electrode and the outer surface of the distal section.

Additionally, in accordance with an embodiment of the present invention the respective thermally conductive material is formed from different material than the respective primary electrode.

Moreover, in accordance with an embodiment of the present invention the respective thermally conductive material and the respective primary electrode are formed as a unitary item, the unitary item having a mass greater than twice a mass of the at least one respective secondary electrode.

Further in accordance with an embodiment of the present invention, the system includes a signal generator configured to generate a pulsed signal to be applied by the respective primary electrode to heart tissue to perform electroporation of the heart tissue.

Still further in accordance with an embodiment of the present invention, the system includes an intracardiac electrogram (IEGM) module configured to receive at least one signal sensed by the at least one respective secondary electrode and generate an IEGM for output to a display device.

There is also provided in accordance with another embodiment of the present invention, a medical system including a catheter including an insertion tube having a distal end, an elongated resilient distal section fixed to the distal end of the insertion tube, the distal section having an outer surface, a plurality of electrode structures disposed on, and bulging above the outer surface of the distal section, and thermally conductive material disposed under the electrode structures, between each of the electrode structures and the outer surface of the distal section, wherein the thermally conductive material is formed from a different material than the electrode structures.

Additionally, in accordance with an embodiment of the present invention the insertion tube is configured for insertion through a blood vessel into a heart of a subject, and wherein the resilient distal section defines a loop when deployed within the heart, and is configured to open and close the loop.

Moreover, in accordance with an embodiment of the present invention the loop has a diameter of between 5 mm and 35 mm.

Further in accordance with an embodiment of the present invention, the system includes a signal generator configured to generate a pulsed signal to be applied by the electrode structures to heart tissue to perform electroporation of the heart tissue.

There is also provided in accordance with still another embodiment of the present invention, a medical method including providing a catheter including an insertion tube having a distal end, a resilient distal section fixed to the distal end of the insertion tube, the distal section having an outer surface and an inner irrigating lumen, and a plurality of electrode structures that bulge above the outer surface, the electrode structures having a plurality of perforations formed therethrough, the electrode structures defining respective hollow sections between respective ones the electrode structures and the outer surface, the perforations being in fluid communication with the irrigating lumen via the hollow sections, and converting the catheter for use in electroporation by injecting a thermally conductive material into the hollow sections via the perforations of the electrodes.

BRIEF DESCRIPTION OF THE DRAWINGS

The present invention will be understood from the following detailed description, taken in conjunction with the drawings in which:

FIGS. 4A-D are cross-sectional views of alternative electrode structures of the lasso catheter through line A:A of FIG. 3;

FIG. 5 is a schematic view of an alternative lasso catheter constructed and operative in accordance with an exemplary embodiment of the present invention; and FIG. 6 is a cross-sectional view of an electrode structure of the lasso catheter through line B:B of FIG. 5.

DESCRIPTION OF EXAMPLE EMBODIMENTS

Overview

Figure 1:
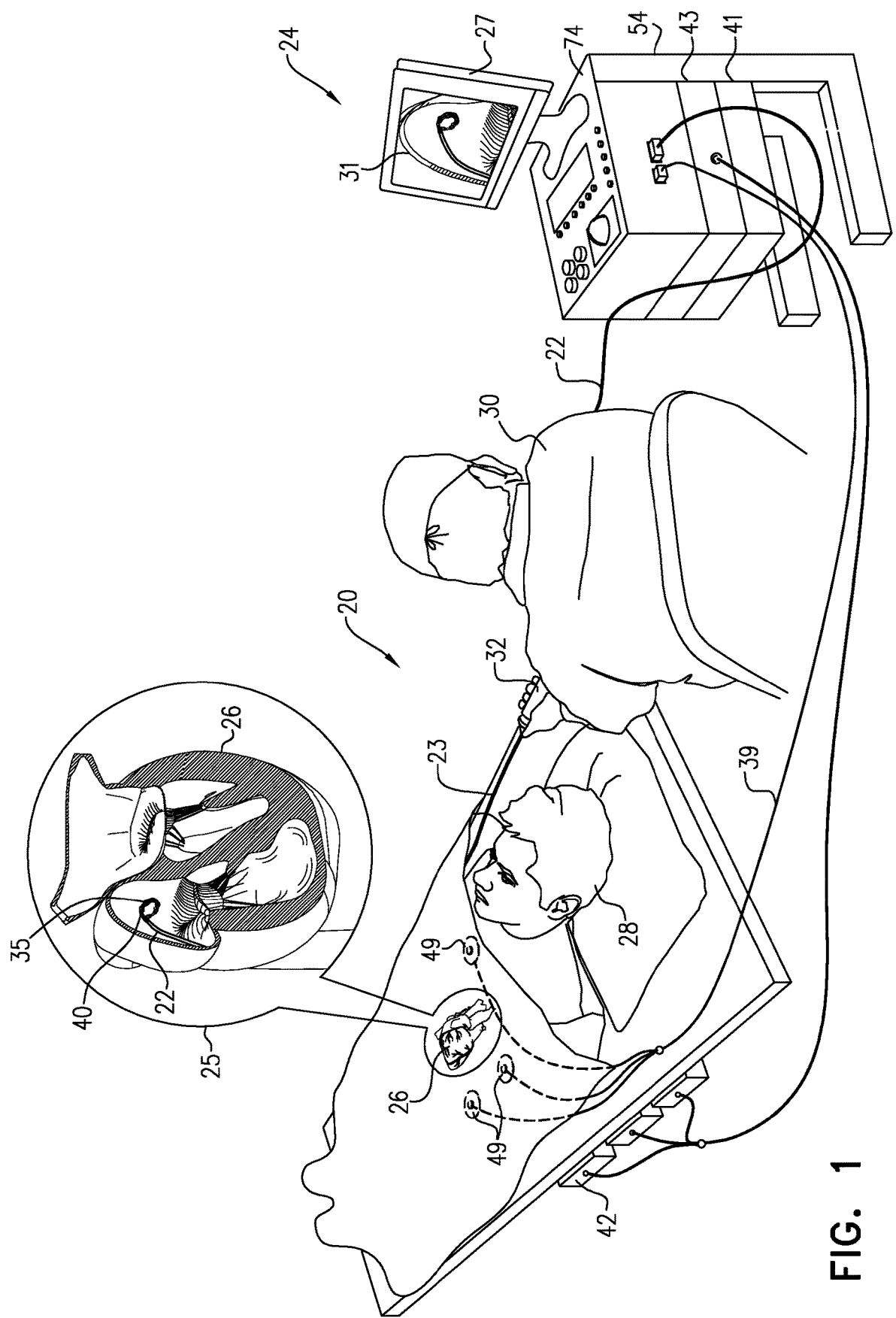
FIG. 1 is a schematic view of a medical system constructed and operative in accordance with an exemplary embodiment of the present invention.

Some catheters, for example, the nMARQ™ catheter of Biosense Webster, Irvine, Calif., provide irrigation via holes in the catheter electrodes. The nMARQ catheter is a lasso-shaped radio-frequency (RF) ablation catheter that includes electrodes disposed along the lasso tube with open irrigation coming from within the tube in the region of the electrodes (e.g., under the electrodes). The irrigation is provided to both reduce heat and dilute the blood to prevent coagulation during RF ablation. Each electrode of the nMARQ bulges above the surface of the lasso tube to ensure that the electrode protrudes above polyurethane which is used to secure the electrodes to the tube at the electrode edges thereby enabling proper contact between the electrodes and heart tissue. The electrodes also have a uniform wall thickness so when the electrode center bulges outwards there is a corresponding hollow section between the tube of the lasso and the inner surface of the electrode. The hollow sections allow irrigation fluid to be pumped into the hollow sections to cool the electrode and exit through holes in the electrodes.

If the same electrodes are used without irrigation (e.g., for electroporation), any heat created (e.g., by the electroporation) will not easily dissipate due to the air gap of the hollow sections between the inner surfaces of the electrodes and the tube, as air is a very poor thermal conductor and the thin wall of the electrode does not provide for much heat capacity. So even though electroporation does not create too much heat, there may be an undesirable local increase in temperature.

Exemplary embodiments of the present invention solve the above problems by providing a catheter having a resilient distal section (e.g., a shapeable loop) with electrode structures placed along the distal section. The electrode structures bulge above the surface of the outer surface of the distal section and include additional thermally conductive material to enhance cooling and increase heat capacity during procedures such as electroporation. The thermally conductive material may be a filler material placed under the electrodes of the electrode structures that is a different material from the rest of the electrode structure. For example, the filler may be a metal such as platinum or a non-metal such as a thermally conductive epoxy. In other exemplary embodiments, the central bulging part of the electrode structure may be constructed to be thicker than the sides of the electrode structure so that the thicker central section of the electrode structure provides thermally conductive material (i.e., the electrode itself) to enhance cooling during procedure such as electroporation.

The term "thermally conductive material," as used in the specification and claims, is defined as a material with a thermal conductivity greater than or equal to 1 Watt per meter Kelvin (W/mK) at 25 degrees Centigrade.

An additional problem associated with electroporation is the need to provide large enough electrodes for applying the current of the electroporation pulse. The same large electrodes which are good for electroporation may not be ideal for use with sensing, for example, for sensing cardiac electrical activity (e.g., intracardiac electrograms (IEGMs) or for sensing position signals using a current or impedance-based position tracking system) as the large electrodes may introduce too much noise in the sensed signals or provide imprecise spatial information due to their size. Providing multiple large electrodes for electroporation and smaller electrodes for sensing along the distal section of the catheter may make the distal section too inflexible.

Exemplary embodiments of the present invention solve the above problems by providing respective ones of the electrode structures with a primary electrode, which may be used for electroporation, and one or more secondary and smaller electrodes, which may be used for sensing. Providing the electrodes for electroporation and sensing on the same electrode structure allows for incorporation of the electroporation and sensing functionality on the catheter while limiting the number of structures on the distal section thereby allowing the distal section to remain sufficiently flexible. In some exemplary embodiments, each electrode structure may include two secondary electrodes, which may be placed on either side of the primary electrode, and may be used to sense position signals, IEGMs and the like. The primary electrode and the secondary electrode(s) may be electrically isolated from each other using a suitable electrically insulating material, for example, an epoxy or any suitable polymer. In some exemplary embodiments, thermally conductive material may be placed below the primary electrode to provide thermal dissipation and heat capacity. In other exemplary embodiments, the primary electrode may be formed to be thicker than the secondary electrode(s) so that the thicker electrode provides at least some of the thermal dissipation. The primary and secondary electrodes may be formed as rings which extend around the distal section of the catheter and are connected together using an electrically insulating material. In other exemplary embodiments, a ring of thermally conductive material may form a ring around the distal section with the primary electrode being placed over the thermally conductive ring and the secondary electrodes being placed either side of the thermally conductive ring. Many other configurations are possible and some are described below with reference to the disclosed exemplary embodiments.

The term "electrically insulating material", as used in the specification and claims, is defined as a material having a volume resistivity greater than one million ohm-centimeters ($\Omega$cm) at 20 degrees Centigrade.

Exemplary embodiments of the present invention provide a medical system, which includes a catheter. The catheter includes an insertion tube and an elongated resilient distal section fixed to a distal end of the insertion tube. The insertion tube is inserted through a blood vessel into a heart of a subject. The resilient distal section defines a loop when deployed within the heart, and is configured to open and close the loop, for example, using an internal resilient member such as a length of metal, e.g., nitinol, which may be manipulated by a physician.

The catheter includes a plurality of electrode structures. Each electrode structure is placed on, and bulges above an outer surface of the distal section. Each electrode structure may include a primary electrode and one or more secondary electrodes extending around the outer surface of the distal section, and electrically insulating material disposed around the outer surface and between each primary electrode and the respective secondary electrode(s). The primary electrode of each electrode structure bulges further above the outer surface than the secondary electrode(s) and the electrically insulating material of that electrode structure.

In some exemplary embodiments, the primary electrode includes a metal ring and the secondary electrode(s) includes a metal ring (or rings). The primary electrode and the respective secondary electrode(s) (i.e. of the same electrode structure) may be connected by the electrically insulating material.

In some exemplary embodiments, the secondary electrodes include two electrodes which are optionally disposed either side of the respective primary electrode (i.e. of the same electrode structure).

The distal section has a direction of elongation. Each primary electrode has a first width measured parallel to the direction of elongation. Each secondary electrode has a second width measured parallel to the direction of elongation. In some exemplary embodiments, the first width is greater than the second width.

Each electrode structure may include thermally conductive material disposed under the respective primary electrode, between the respective primary electrode and the outer surface of the distal section. In some exemplary embodiments, the thermally conductive material is formed from different material than the primary electrode. In other exemplary embodiments, the thermally conductive material and the primary electrode are formed as a unitary item. The unitary item forming the primary electrode may have a mass greater than twice a mass of each secondary electrode.

The medical system may include a signal generator which generates a pulsed signal to be applied by the one or more of the primary electrodes to heart tissue to perform electroporation of the heart tissue. The medical system may include an IEGM module configured to receive at least one signal sensed by the secondary electrode(s) and generate an IEGM (or IEGMs) for output to a display device.

In some exemplary embodiments, each electrode structure includes a single electrode with thermally conductive material disposed under the electrode structures between each electrode structure and the outer surface of the distal section. The thermally conductive material is formed from a different material than the electrode structures.

In some exemplary embodiments, an irrigated catheter may be converted for use with electroporation as follows. The method includes providing a catheter comprising an insertion tube and a resilient distal section fixed to a distal end of the insertion tube. The distal section has an outer surface and an inner irrigating lumen, and electrode structures that bulge above the outer surface. The electrode structures have perforations formed therethrough, and define respective hollow sections between respective ones the electrode structures and the outer surface. The perforations are in fluid communication with the irrigating lumen via the hollow sections. The method includes converting the catheter for use in electroporation by injecting a thermally conductive material into the hollow sections via the perforations of the electrodes, and generally, but not necessarily, precluding the catheter from providing irrigation.

System Description

Figure 2:
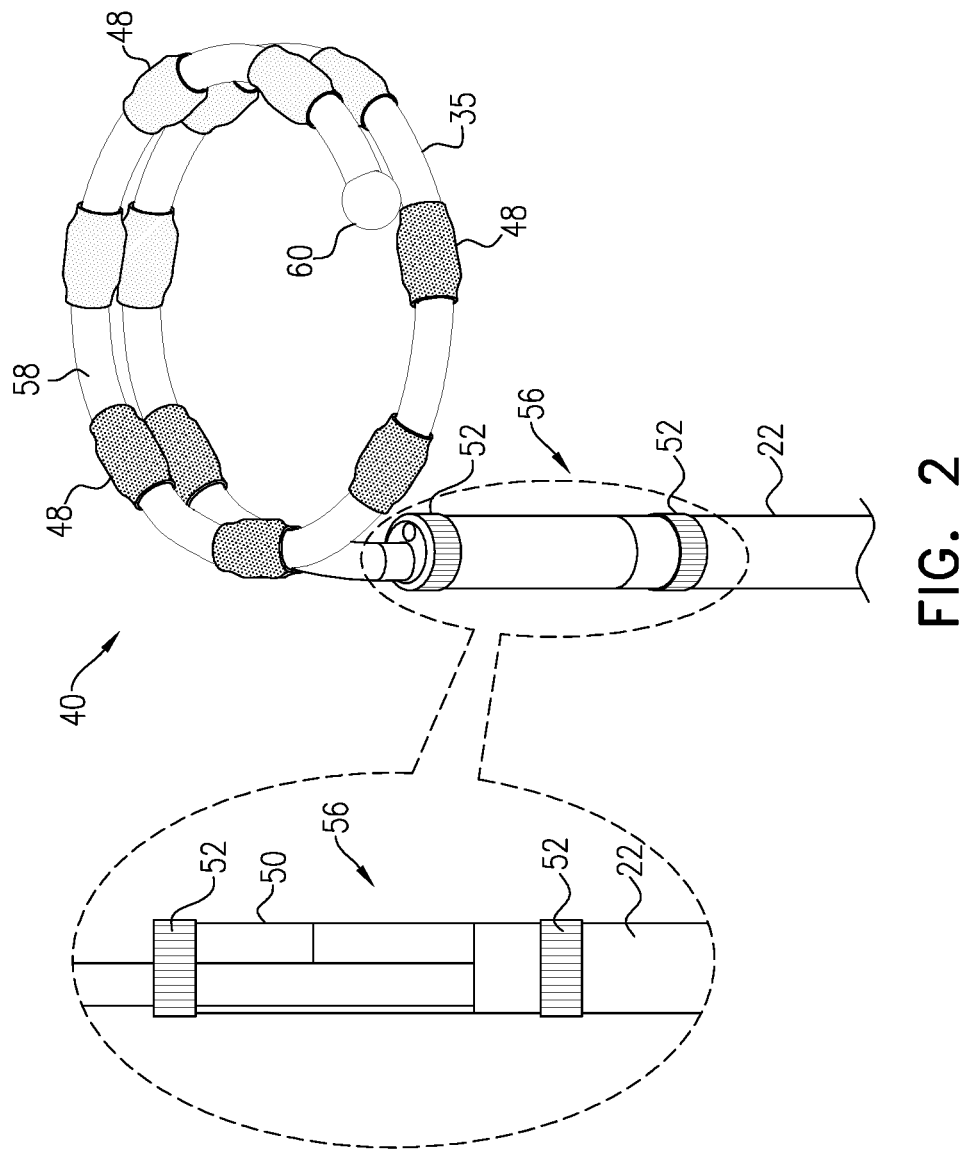
FIG. 2 is a schematic view of a lasso catheter in a closed configuration constructed and operative in accordance with an exemplary embodiment of the present invention.

Reference is now made to FIG. 1, which is a schematic view of a medical system 20 constructed and operative in accordance with an exemplary embodiment of the present invention. Reference is also made to FIG. 2, which is a schematic view of a lasso catheter 40 in a closed configuration constructed and operative in accordance with an exemplary embodiment of the present invention.

The system 20 includes the catheter 40 configured to be inserted into a body part of a living subject (e.g., a patient 28). A physician 30 navigates the catheter 40, to a target location in a heart 26 of the patient 28 (inset 25), by manipulating a deflectable element of an insertion tube 22 of the catheter 40, using a manipulator 32 near a proximal end of the catheter 40, and/or deflection from a sheath 23. In this, or any suitable manner, the insertion tube 22 is configured for insertion through a blood vessel into a heart of a subject. In the pictured embodiment, physician 30 uses catheter 40 to perform electro-anatomical mapping of a cardiac chamber and ablation of cardiac tissue.

Catheter 40 includes an elongated resilient distal section 35 (e.g., an adjustable loop), which is inserted in a straight configuration, through sheath 23, and only after the catheter 40 exits sheath 23 does the elongated resilient distal section 35 regain its intended functional shape. By containing elongated resilient distal section 35 in a straight configuration, sheath 23 also serves to minimize vascular trauma on its way to the target location.

Catheter 40 includes a plurality of electrode structures 48 (only some labeled for the sake of simplicity) including electrodes for sensing electrical activity and/or applying ablation and/or electroporation power to ablate and/or electroporate tissue of the body part. Catheter 40 may incorporate a magnetic sensor 50 (shown in a cut-away section of the insertion tube 22 on the left side of FIG. 2) at the distal edge of the insertion tube 22 (i.e., at the proximal edge of the elongated resilient distal section 35). The magnetic sensor 50 may be a Single-Axis Sensor (SAS), or a Dual-Axis Sensor (DAS), or a Triple-Axis Sensor (TAS) by way of example only, based for example on sizing considerations. The catheter 40 may also include one or more electrodes 52 disposed on the distal edge of the insertion tube 22, for example, on either side of the magnetic sensor 50. The electrode(s) 52, magnetic sensor 50, and the electrodes of the electrode structures 48 disposed on the elongated resilient distal section 35 are connected by wires running through insertion tube 22 to various driver circuitries in a console 24.

In some exemplary embodiments, system 20 comprises a magnetic-sensing sub-system to estimate a position of the elongated resilient distal section 35 of catheter 40 inside a cardiac chamber of heart 26. Patient 28 is placed in a magnetic field generated by a pad containing one or more magnetic field generator coils 42, which are driven by a unit 43. The magnetic fields generated by coil(s) 42 transmit alternating magnetic fields into a region where the body-part is located. The transmitted alternating magnetic fields generate signals in the magnetic sensor 50, which are indicative of position and/or direction of the distal end of the catheter 40. The generated signals are transmitted to console 24 and become corresponding electrical inputs to processing circuitry 41.

In some exemplary embodiments, the processing circuitry 41 uses position-signals received from the electrodes 52 and/or the electrodes of the electrode structures 48, and/or the magnetic sensor 50 to estimate a position of the catheter 40 inside an organ, such as inside a cardiac chamber. In some embodiments, the processing circuitry 41 correlates the position signals received from the electrodes with previously acquired magnetic location-calibrated position signals, to estimate the position of the catheter 40 inside the organ. The position coordinates of the electrodes may be determined by the processing circuitry 41 based on, among other inputs, measured impedances, or on proportions of current distribution, between the electrodes and body surface electrodes 49.

The method of position sensing using current distribution measurements and/or external magnetic fields is implemented in various medical applications, for example, in the Carto® system, produced by Biosense Webster Inc. (Irvine, Calif.), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publication Nos. 2002/0065455 A1, 2003/0120150 A1 and 2004/0068178 A1.

The Carto®3 system applies an Advanced Catheter Location (ACL) impedance-based position-tracking method. In some exemplary embodiments, using the ACL method, the processing circuitry 41 is configured to create a mapping (e.g., current-position matrix (CPM)) between indications of electrical impedance and positions in a magnetic coordinate frame of the magnetic field generator coils 42. The processing circuitry 41 estimates the positions of the electrodes by performing a lookup in the CPM.

Other methods of determining the location of the distal end of the catheter 40 may be used, for example, based on ultrasonic transducers and receivers, using imaging techniques such as ultrasound or MRI or CT scans which may include disposing radiopaque tags on the catheter 40.

The processing circuitry 41, typically part of a general-purpose computer, is further connected via a suitable front end and interface circuits 44, to receive signals from the body surface-electrodes 49. Processing circuitry 41 is connected to body surface-electrodes 49 by wires running through a cable 39 to the chest of patient 28.

In some exemplary embodiments, processing circuitry 41 renders to a display device 27, a representation 31 of at least a part of the catheter 40 and a mapped body-part, responsively to computed position coordinates of the catheter 40.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The medical system 20 may also include a signal generator 54 (such as an RF signal generator) configured to be connected to the catheter 40, and apply an electrical signal to electrodes of the electrode structures 48 to perform RF ablation and/or electroporation.

The example illustrations shown in FIGS. 1 and 2 are chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation and/or electroporation of tissue of heart 26.

The medical system 20 has been described with reference to catheter 40 having a lasso-shaped elongated resilient distal section 35. The catheter 40 may be implemented with any suitable shaped elongated resilient distal section 35, for example, but not limited to, a multi-spline catheter.

Figure 3:
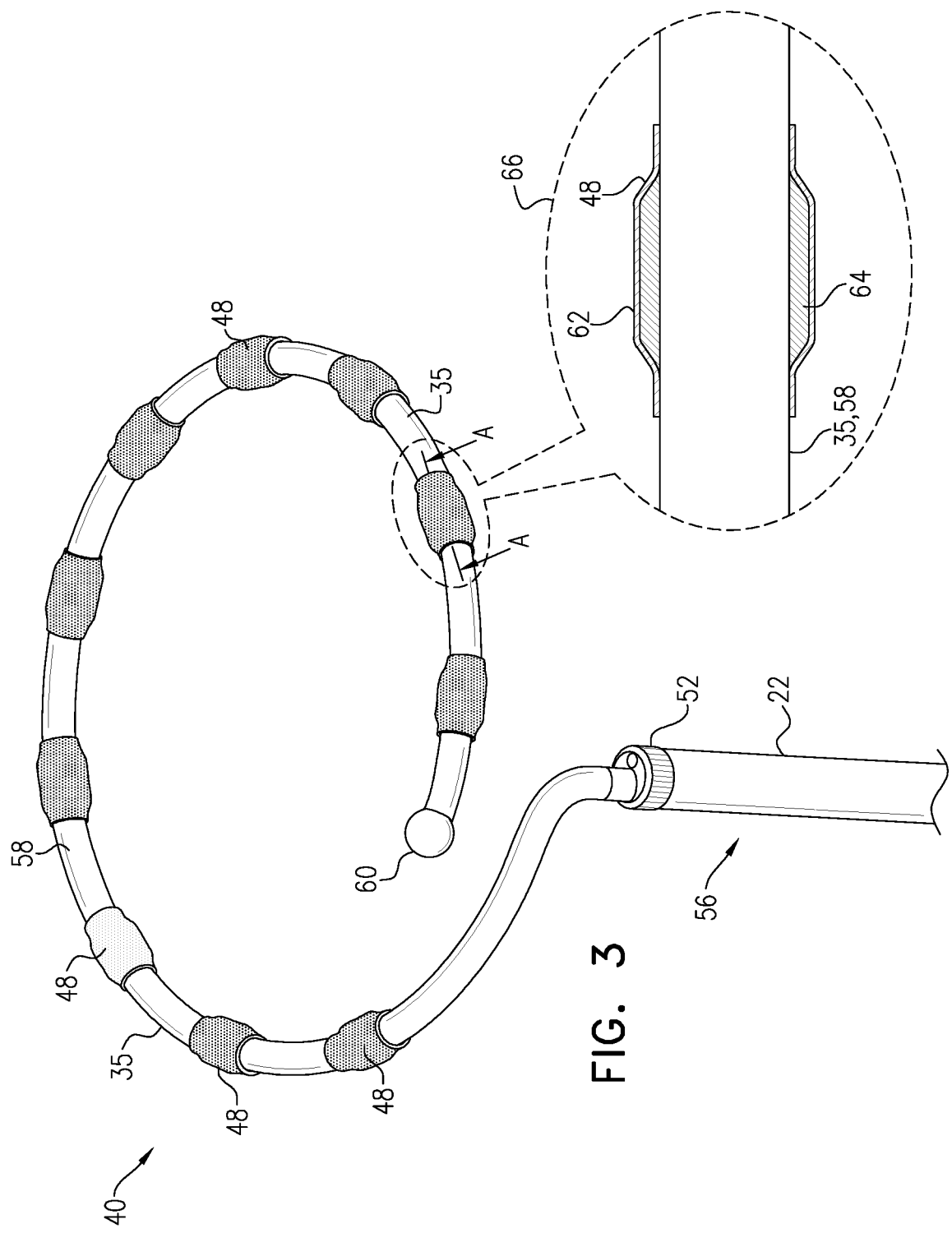
FIG. 3 is a schematic view of the lasso catheter of FIG. 2 in an open configuration.

Reference is now made to FIG. 3, which is a schematic view of the lasso catheter 40 of FIG. 2 in an open configuration. Reference is also made to FIG. 2.

A distal end 56 of the insertion tube 22 typically comprises a deflectable section and a distal edge including the electrodes 52 with the magnetic sensor 50 disposed in between the two electrodes. The distance between the center of the two electrodes 52 may be any suitable distance, such as in the range of 5 mm to 20 mm, e.g., 11 mm. The magnetic sensor 50 (e.g., a magnetic coil sensor) may be disposed in any suitable location. In the example of FIG. 2, the magnetic sensor 50 is shown as being closer to the distal one of the electrodes 52. The insertion tube 22 may have any suitable outer diameter, for example, in the range of 1 to 6 mm, e.g., 2.5 mm.

The elongated resilient distal section 35 is fixed to the distal end 56 of the insertion tube 22. The elongated resilient distal section 35 has an outer surface 58. The elongated resilient distal section 35 may be comprised of any suitable material(s), for example, a flexible polymer such as polyurethane, or polyether block amide. The resilient distal section 35 defines a loop when deployed within the heart and is configured to open and close (or tighten and loosen) the loop. The term "loop", as used in the specification and claims, is defined as the elongated resilient distal section 35 bending around a curve by at least 180 degrees and forming a closed curve, or a partially overlapping curve, or a partially open loop.

The loop shape may be formed by a resilient or deflectable element (not shown), such as a nitinol spine, disposed inside a lumen of the elongated resilient distal section 35, which allows elongated resilient distal section 35 to be straight during insertion into the heart 26 (FIG. 1) and form a loop once the elongated resilient distal section 35 exits from the sheath 23 (FIG. 1). The loop may be contracted by pulling on the resilient element, for example, using the manipulator 32 (FIG. 1). In some exemplary embodiments, the elongated resilient distal section 35 may be formed as an inflatable element.

The open loop (FIG. 3) and the closed loop (FIG. 2) may have any suitable diameter. In some exemplary embodiments, the open loop has a diameter of between 10 mm and 35 mm, and the closed loop has a diameter between 5 mm and 25 mm. In some exemplary embodiments, the distal section has an open diameter of 25.4 mm and a closed diameter of 15.24 mm.

Each electrode structure 48 is disposed on, and bulges above the outer surface 58 of the elongated resilient distal section 35. The electrode structures 48 (only some labeled for the sake of simplicity) may be connected to the elongated resilient distal section 35 using a suitable adhesive and/or using polyurethane, which is used to secure the edges of the electrode structures 48 to the elongated resilient distal section 35.

The catheter 40 may include any suitable number of electrode structures 48 depending on the width of each electrode structure 48, the length of the elongated resilient distal section 35, and the desired flexibility of the distal section 35. More electrode structures 48 may make the distal section 35 too inflexible. FIGS. 2 and 3 show ten electrode structures 48 disposed on the distal section. In other exemplary embodiments, the number of electrode structures 48 disposed on the distal section 35 may include any suitable number, for example, in the range of 4 to 30.

The electrode structures 48 may be spaced evenly or unevenly along the distal section 35. In some exemplary embodiments, the center-to-center spacing between electrode structures 48 as measured along the arc is 7 mm, but may take any suitable value, for example, in the range of 3 mm to 30 mm. The distance from the center of the most distal electrode structure 48 to a tip 60 of the distal section 35 may be any suitable value, for example, in the range of 1 mm to 20 mm, e.g., 7 mm.

In some exemplary embodiments, as shown in an inset 66 (which shows a cross-sectional view through line A:A of FIG. 3), each electrode structure 48 includes one electrode 62 with a thermally conductive material 64 disposed between the electrode 62 and the outer surface 58. The thermally conductive material 64 may be any suitable thermally conductive material, for example, but not limited to, platinum, palladium, gold, or thermally conductive epoxy. In some exemplary embodiments, the thermally conductive material 64 is first wrapped around the outer surface 58 of the elongated resilient distal section 35, and then the electrode 62 is wrapped around the thermally conductive material 64. In other exemplary embodiments, the electrode 62 is first fixed around the outer surface 58 (as a single piece or from two halves subsequently joined together) and then the thermally conductive material 64 is injected below the electrode 62 through a hole in the electrode 62.

Reference is now made to FIGS. 4A-D, which are cross-sectional views of alternative electrode structures 48 of the lasso catheter 40 through line A:A of FIG. 3. The common features of the various electrode structures 48 shown in FIGS. 4A-D are first described below.

Each electrode structure 48 comprises a respective primary electrode 68 and at least one respective secondary electrode 70 extending around the outer surface 58. Each electrode structure 48 also includes respective electrically insulating material 72 disposed around the outer surface 58 and between the respective primary electrode 68 and the respective secondary electrode(s) 70. The term "respective" with reference to the primary electrode 68, the secondary electrode(s) 70, and the electrically insulating material 72, is used to described the primary electrode 68, the secondary electrode(s) 70 and the electrically insulating material 72 of the same electrode structure 48. The respective primary electrode 68 bulges further above the outer surface 58 than the respective secondary electrode(s) 70 and the respective electrically insulating material 72.

In some exemplary embodiments, each electrode structure 48 includes two secondary electrodes 70, which are optionally disposed either side of the respective primary electrode 68.

As previously mentioned, a problem associated with electroporation is the need to provide large enough electrodes for applying the current of the electroporation signal. The same large electrodes which are good for electroporation may not be ideal for use with sensing, for example, for sensing cardiac electrical activity (e.g., intracardiac electrograms (IEGMs) or for sensing position signals using a current or impedance-based position tracking system) as the large electrodes may introduce too much noise in the sensed signals. Providing multiple large electrodes for electroporation and smaller electrodes for sensing along the distal section of the catheter may make the distal section too inflexible. Therefore, in some exemplary embodiments, each secondary electrode 70 is typically narrower than the primary electrode 68 allowing the primary electrode 68 to be used for electroporation and the secondary electrode(s) 70 to be used for sensing. As the primary electrode 68 and the secondary electrodes 70 are included in a single structure of the electrode structure 48, large electrodes for electroporation and smaller electrodes for sensing may be provided along the distal section 35 of the catheter 40 without making the catheter 40 too inflexible.

In some exemplary embodiments, the signal generator 54 (FIG. 1) is configured to generate a pulsed signal to be applied by one or more of the primary electrodes 68 to heart tissue to perform electroporation of the heart tissue. In some embodiments, the medical system 20 includes an intracardiac electrogram (IEGM) module 74 (FIG. 1) configured to receive at least one signal sensed by one or more of the secondary electrodes 70 and generate one or more IEGMs for output to the display device 27 (FIG. 1).

In some exemplary embodiments, each primary electrode 68, and each secondary electrode 70 is formed from a metal strip which is wrapped around the outer surface 58 of the elongated resilient distal section 35 forming corresponding metal rings. In other embodiments, each primary electrode 68, and each secondary electrode 70 may be formed from half rings which are joined together around the outer surface 58. The primary electrode 68 and the secondary electrode(s) 70 of one of the electrode structures 48 may be connected together by the electrically insulating material 72. The electrically insulating material 72 may also serve as the adhesive to glue the primary electrode 68 to the secondary electrode(s) 70. In other exemplary embodiments, a suitable adhesive may be used to connect the primary electrode 68, the secondary electrode(s) 70, and the electrically insulating material 72.

In some exemplary embodiments, a retention piece (or pieces) of material may be used to hold the primary electrode 68 to the secondary electrode(s) 70. The electrically insulating material 72 (e.g., epoxy) may then be added between the primary electrode 68 and the secondary electrode(s) 70 thereby further adhering the primary electrode 68 with the secondary electrode(s) 70. After the electrically insulating material 72 has set, the retention piece(s) may be removed.

In some exemplary embodiments (see FIG. 4B), the electrically insulating material 72 may comprise a strip of material which is wrapped around the outer surface 58 of the elongated resilient distal section 35.

Figure 4A:
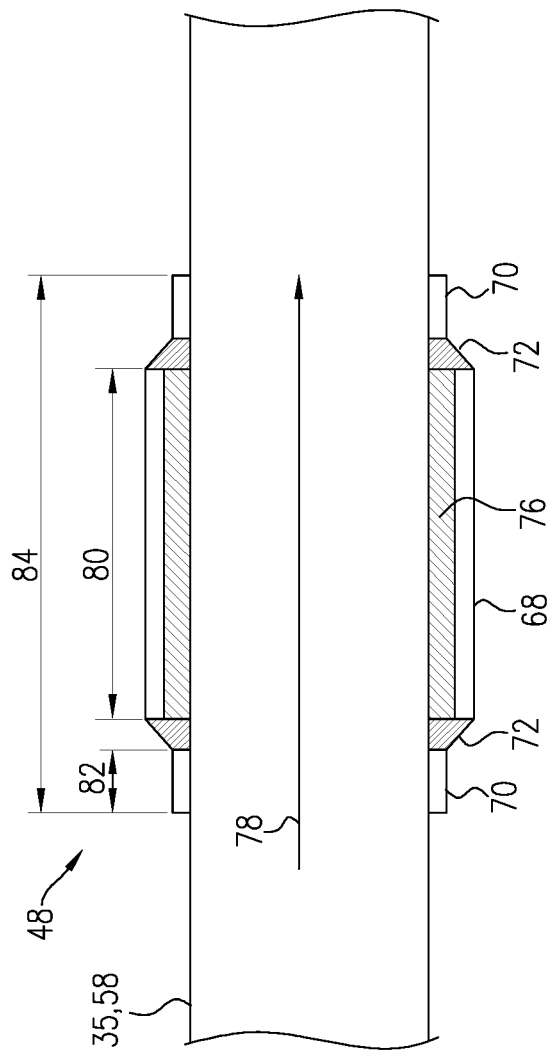
Figure 4B:
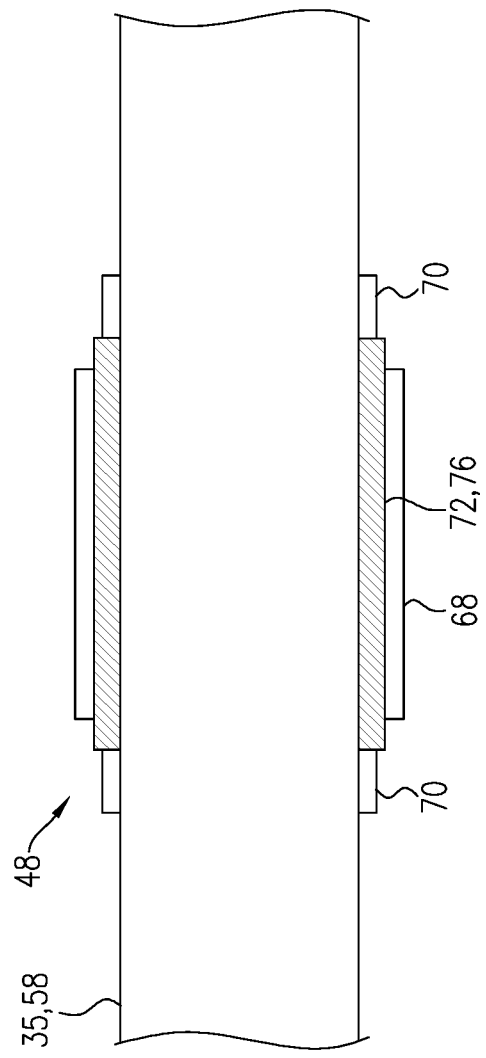

In some exemplary embodiments, each electrode structure 48 includes respective thermally conductive material 76 disposed under the respective primary electrode 68, between the respective primary electrode 68 and the outer surface 58 of the distal section 35. In some exemplary embodiments, the thermally conductive material 76 forms part of the primary electrode 68 (as shown in FIGS. 4C and 4D). In other exemplary embodiments, the thermally conductive material 76 is placed as a separate element (e.g., a ring disposed around the outer surface 58) under the primary electrode 68 as shown in FIGS. 4A and 4B. In some exemplary embodiments, the thermally conductive material 76 also functions as the electrically insulating material 72 as shown in FIG. 4B.

Reference is now made to FIG. 4A. Typical dimensions of the electrode structures 48 are now described with reference to FIG. 4A. The dimensions described below may also be applied to other exemplary embodiments, for example, the exemplary embodiments described with reference to FIGS. 4B-D. Notwithstanding the example dimensions described below, the dimensions of the electrode structures 48 may comprise any suitable values.

The elongated resilient distal section 35 has a direction of elongation 78. The primary electrode 68 has a width 80 measured parallel to the direction of elongation 78. Each secondary electrode 70 has a width 82 measured parallel to the direction of elongation 78. The width 80 is greater than the width 82. In some exemplary embodiments, the width 80 is at least twice the size of the width 82. In some exemplary embodiments the width 80 is in a range of 2 mm to 8 mm and the width 82 is in a range of 0.1 mm to 1 mm. Each electrode structure 48 has a total width 84 measured parallel to the direction of elongation 79 of between 2.5 and 10 mm.

FIG. 4A shows that the thermally conductive material 76 is formed from different material than the primary electrode 68. The thermally conductive material 76 may be formed as a rectangular strip wrapped around the elongated resilient distal section 35 with the primary electrode 68 being wrapped on top of the thermally conductive material 76. In some exemplary embodiments, the thermally conductive material 76 and/or primary electrode 68 may be formed as two half rings which are connected around the elongated resilient distal section 35. The secondary electrode 70 are connected to the primary electrode 68 via the electrically insulating material 72, which may also act as adhesive to connect the primary electrode 68 with the secondary electrode(s) 70. The wall thickness of the primary electrode 68 and the secondary electrode 70 may have any suitable value, for example, in the range of 0.01 mm to 0.25 mm. The thickness of the thermally conductive material 76 may have any suitable value, for example, in the range of 0.01 mm to 0.25 mm.

Reference is now made to FIG. 4B. FIG. 4B shows that the electrically insulating material 72 and the thermally conductive material 76 are the same element. The electrically insulating material 72 and thermally conductive material 76 may be comprised of epoxy, such as boron nitride or diamond doped epoxy and have a thickness in the range of 0.01 mm to 0.25 mm. The primary electrode 68 is disposed partially over the electrically insulating material 72 and the thermally conductive material 76. The secondary electrodes 70 are placed on either side of the electrically insulating material 72 and thermally conductive material 76. The dimensions of the primary electrode 68 and the secondary electrode 70 are substantially the same as mentioned with reference to FIG. 4A.

Reference is now made to FIGS. 4C and 4D. FIGS. 4C and 4D show that the thermally conductive material 76 and the primary electrode 68 are formed as a unitary item, whereby the thicker primary electrode 68 provides dissipation of heat formed during electroporation. In some exemplary embodiments, the unitary item may have a mass greater than twice a mass of one of the secondary electrodes 70 of that electrode structure 48. The wall thickness of the primary electrode 68 may have any suitable value, for example, in the range of 0.025 mm to 0.5 mm. The wall thickness of the secondary electrode 70 may have any suitable value, for example, in the range of 0.025 mm to 0.5 mm. In some exemplary embodiments, the wall thickness of the primary electrode 68 is at least double the wall thickness of the secondary electrode 70. The primary electrode 68 and the secondary electrode 70 shown in FIG. 4C may each be formed as flat electrodes which are wound around the outer surface 58 to form rings or as two half rings which are connected together around the elongated resilient distal section 35. The primary electrode 68 shown in FIG. 4D has anon-uniform surface and bulges further away from the outer surface 58 towards the center of the primary electrode 68.

Reference is now made to FIG. 5, which is a schematic view of an alternative lasso catheter 86 constructed and operative in accordance with an exemplary embodiment of the present invention. Reference is also made to FIG. 6, which is a cross-sectional view of one of the electrode structures 48 of the lasso catheter 86 through line B:B of FIG. 5. The lasso catheter 86 is substantially the same as the catheter 40 of FIGS. 1-4 except for the following differences. The elongated resilient distal section 35 includes an inner irrigating lumen 94 (FIG. 6). Each electrode structure 48 (only some labeled for the sake of simplicity) includes at least one irrigation hole (perforation) 92 (only some labeled for the sake of simplicity) formed therethrough. The electrode structures 48 define respective hollow sections 96 between respective ones the electrode structures 48 and the outer surface 58. The perforations 92 are in fluid communication with the irrigating lumen 94 via the hollow sections 96.

The lasso catheter 86 may be converted from an irrigated catheter to a non-irrigated catheter for performing electroporation as follows. Thermally conductive material 90 is injected into the hollow section 96 under each of the electrode structures 48 of the lasso catheter 86, between each electrode structure 48 and the outer surface 58 of the distal section 35. The placement of the thermally conductive material 90 generally precludes the lasso catheter 86 from providing irrigation via the electrode structures 48. The thermally conductive material 90 may be injected below the electrode structures 48 via the perforations 92. The thermally conductive material 90 is generally formed from a different material (e.g., epoxy or platinum) than the electrode structures 48, but may be formed from the same material as the electrode structures 48.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A medical system comprising a catheter including:
   an insertion tube having a distal end;
   an elongated resilient distal section fixed to the distal end of the insertion tube, the distal section having an outer surface; and
   a plurality of electrode structures, each electrode structure being an annular structure disposed around, and bulging above the outer surface of the distal section, each electrode structure comprising a respective primary electrode and at least one respective secondary electrode rigidly connected to the respective primary electrode with electrically insulating material disposed between the respective primary electrode and the at least one respective secondary electrode, the respective primary electrode bulging further above the outer surface than the at least one respective secondary electrode and the respective electrically insulating material; and
   wherein the at least one respective secondary electrode includes an outer annular surface, an inner annular surface and two side surfaces and wherein the electrically insulating material is disposed over one of the two side surfaces and extends to the respective primary electrode to cover the one of the two side surfaces and fill a volume between the one of the two side surfaces and the respective primary electrode.

2. The system according to claim 1, wherein the insertion tube is configured for insertion through a blood vessel into a heart of a subject, and wherein the resilient distal section defines a loop when deployed within the heart, and is configured to open and close the loop.

3. The system according to claim 2, wherein the loop has a diameter of between 5 mm and 35 mm.

4. The system according to claim 1, further comprising an adhesive material formed from electrically insulating material between the respective primary electrode and the at least one respective secondary electrode, wherein the respective primary electrode includes a metal ring and the at least one respective secondary electrode includes at least one metal ring, the respective primary electrode and the at least one respective secondary electrode being connected by the respective electrically insulating material.

5. The system according to claim 1, wherein the at least one respective secondary electrode comprises two respective electrodes.

6. The system according to claim 5, wherein the two respective electrodes are disposed either side of the respective primary electrode.

7. The system according to claim 5, wherein the distal section has a direction of elongation, the respective primary electrode having a first width measured parallel to the direction of elongation, each of the two respective electrodes having a second width measured parallel to the direction of elongation, the first width being greater than the second width.

8. The system according to claim 7, wherein the first width is at least twice the size of the second width.

9. The system according to claim 7, wherein the first width is in a range of 2 mm to 8 mm and the second width is in a range of 0.1 mm to 1 mm.

10. The system according to claim 1, wherein the distal section has a direction of elongation, each electrode structure having a width measured parallel to the direction of elongation of between 2.5 mm and 10 mm.

11. The system according to claim 1, wherein each electrode structure includes respective thermally conductive material disposed under the respective primary electrode, between the respective primary electrode and the outer surface of the distal section, wherein the thermally conductive material is selected from a group including: platinum, palladium, gold, and thermally conductive epoxy.

12. The system according to claim 11, wherein the respective thermally conductive material is formed from different material than the respective primary electrode.

13. The system according to claim 11, wherein the respective thermally conductive material and the respective primary electrode are formed as a unitary item, the unitary item having a mass greater than twice a mass of the at least one respective secondary electrode.

14. The system according to claim 1, further comprising a signal generator configured to generate a pulsed signal to be applied by the respective primary electrode to heart tissue to perform electroporation of the heart tissue.

15. The system according to claim 14, further comprising an intracardiac electrogram (IEGM) module configured to receive at least one signal sensed by the at least one respective secondary electrode and generate an IEGM for output to a display device.

16. The medical system of claim 1, wherein each of the plurality of electrode structures forms a single rigid unbendable structure.

* * * * *